United States Patent
Connell et al.

[11] Patent Number: 6,124,035
[45] Date of Patent: Sep. 26, 2000

[54] HIGH TEMPERATURE TRANSFER MOLDING RESINS

[75] Inventors: John W. Connell, Yorktown; Joseph G. Smith, Jr., Smithfield; Paul M. Hergenrother, Yorktown, all of Va.

[73] Assignee: The United States of America as represented by the Administrator of the National Aeronautics and Space Administration, Washington, D.C.

[21] Appl. No.: 09/310,686

[22] Filed: Apr. 13, 1999

[51] Int. Cl.[7] .......................... C07D 209/48; C08G 8/02; C08G 73/10

[52] U.S. Cl. ................... 428/411.1; 428/524; 428/473.5; 528/125; 528/128; 528/229; 528/170; 528/353; 548/473; 548/476

[58] Field of Search .................... 548/473, 476; 428/473.5, 524, 411.1; 528/125, 128, 170, 229

[56] References Cited

U.S. PATENT DOCUMENTS 5,412,066  5/1995  Hergenrother et al. ................. 528/353
5,606,014  2/1997  Connell et al. ......................... 528/353

*Primary Examiner*—Joseph McKane
*Assistant Examiner*—Jane C. Oswecki
*Attorney, Agent, or Firm*—Hillary W. Hawkins

[57] ABSTRACT

High temperature resins containing phenylethynyl groups that are processable by transfer molding have been prepared. These phenylethynyl containing oligomers were prepared from aromatic diamines containing phenylethynyl groups and various ratios of phthalic anhydride and 4-phenylethynlphthalic anhydride in glacial acetic acid to form a mixture of imide compounds in one step. This synthetic approach is advantageous since the products are a mixture of compounds and consequently exhibit a relatively low melting temperature. In addition, these materials exhibit low melt viscosities which are stable for several hours at 210–275° C., and since the thermal reaction of the phenylethynyl group does not occur to any appreciable extent at temperatures below 300° C., these materials have a broad processing window. Upon thermal cure at ~300–350° C., the phenylethynyl groups react to provide a crosslinked resin system. These new materials exhibit excellent properties and are potentially useful as adhesives, coatings, films, moldings and composite matrices.

7 Claims, 2 Drawing Sheets

HIGH TEMPERATURE TRANSFER MOLDING RESINS

CROSS-REFERENCE

This patent application is related to commonly owned co-pending patent application Ser. No. 09/290295, filed Apr. 13, 1999, entitled "PHENYLETHYNYL CONTAINING REACTIVE ADDITIVES".

ORIGIN OF THE INVENTION

The invention described herein was made by employees of the United States Government and may be manufactured and used by or for the Government or government purposes without payment of any royalties therein or thereof.

BACKGROUND OF THE INVENTION

A variety of monomers, oligomers and polymers containing ethynyl (acetylenic) and substituted ethynyl (i.e., phenylethynyl) groups have been reported. The ethynyl groups in the polymer are either pendent to the chain, in the chain or at the chain ends. Many of these materials have been used to prepare coatings, moldings, adhesives and composites [P. M. Hergenrother, "Acetylene Terminated Prepolymers" in Encyclopedia of Polymer Science and Engineering, John Wiley and Sons, New York, Vol. 1, 61 (1985)]. Good processability by either solution casting and/or compression molding has been observed for the ethynyl and substituted ethynyl containing materials. In general, thermally cured ethynyl and substituted ethynyl containing materials exhibit a favorable combination of physical and mechanical properties. Some ethynyl endcapped materials such as the Thermid® resins are commercially available (National Starch and Chemical Co., Bridgewater, N.J. 08807). Other systems such as acetylene terminated sulfones have undergone extensive evaluation as matrix resins [M. G. Maximovich, S. C. Lockerby, F. E. Arnold and G. A. Loughran, Sci. Adv. Matls. Proc. Eng. Ser., 23, 490 (1978) and G. A. Loughran, A. Wereta and F. E. Arnold, U.S. Pat. No. 4,131,625, December 1978 to U.S. Air Force]. Phenylethynyl containing amines have been used to terminate imide oligomers [F. W. Harris, A. Pamidimuhkala, R. Gupta, S. Das, T. Wu, G. Mock, Poly. Prep., 24 (2), 325, 1983; F. W. Harris, A. Pamidimuhkala, R. Gupta, S. Das, T. Wu, G. Mock, Macromol. Sci.-Chem., A21 (8&9), 1117 (1984); C. W. Paul, R. A. Shultz, and S. P. Fenelli, "High Temperature Curing Endcaps for Polyimide Oligomers" in Advances in Polyimide Science and Technology, (Ed. C. Feger, M. M. Khoyasteh, and M. S. Htoo), Technomic Publishing Co., Inc., Lancaster, Pa., 1993, p. 220; R. G. Bryant, B. J. Jensen, P. M. Hergenrother, Poly. Prepr., 34(1), 566, 1993]. Imide oligomers terminated with ethynyl phthalic anhydride [P. M. Hergenrother, Poly. Prepr., 21(1), 81, 1980], substituted ethynyl phthalic anhydride [S. Hino, S. Sato, K. Kora, and O. Suzuki, Jpn. Kokai Tokyo Koho Japanese Patent # 63,196,564. Aug. 15, 1988; Chem. Abstr., 115573w, 110, (1989)] and phenylethynyl containing phthalic anhydrides have been reported. Imide oligomers containing pendent substituted ethynyl groups [F. W. Harris, S. M. Padaki, and S. Varaprath, Poly. Prepr., 21(1), 3, 1980 (abstract only); B. J. Jensen, P. M. Hergenrother and G. Nwokogu, Polymer, 34(3), 630, 1993; B. J. Jensen and P. M. Hergenrother, U.S. Pat. No. 5,344,982 (Sep. 6, 1994)] have been reported. See also J. E. McGrath and G. W. Meyer, U.S. Pat. No. 4,493,002 (Feb. 20, 1996), J. G. Smith, Jr. Adhesion Society Proceedings, Vol. 19, 29–32 (1996) and J. W. Connell, J. G. Smith, Jr. and P. M. Hergenrother, Society for the Advancement of Materials and Process Engineering Proceedings, Vol. 41, 1102–1112 (1996).

High temperature resins are used in a variety of aerospace and non-aerospace applications. Generally these materials require high pressures (>200 psi) to form adhesive bonds, well-consolidated moldings or fiber reinforced composite laminates. If these systems could be modified so as to retain the high performance characteristics yet be processable using resin transfer techniques, then the cost of manuacturing would be substantially reduced since an autoclave would not be needed.

It is a primary object of the present invention to provide novel phenylethynyl containing compounds that are processable via resin transfer techniques. These materials exhibit the proper combination of properties to allow processing under resin transfer molding conditions. In addition, upon thermal curing these materials exhibit sufficient thermal stability, toughness and mechanical properties so as to be useful as adhesives, coatings, films, filled and unfilled moldings and composite matrix resins in high performance applications.

Another object of the present invention is to provide novel polymeric materials that are useful as adhesives, coatings, films, moldings and composite matrices.

Another object of the present invention is the composition of several new phenylethynyl containing imide compounds.

SUMMARY OF THE INVENTION

According to the present invention the forgoing and additional objects are obtained by synthesizing imide compounds containing phenylethynyl groups. These materials are synthesized by reacting aromatic diamines containing phenylethynyl groups with various ratios of phthalic anhydride (PA) and 4-phenylethynyl phthalic anhydride (PEPA). These compounds were evaluated for thermal and rheological properties and for processability. These materials have advantages over state-of-the-art materials that are processable by resin transfer techniques, such as epoxies and bismaleimides in that they have superior thermal stability and can therefore be used in higher temperature applications.

The unique and unexpected combination of properties exhibited by these resins includes; ease of synthesis (one-step, quantitative yield reaction), relatively low melting temperature (~182° C.), low melt viscosity (<1 poise at ~270° C.), excellent melt stability (>2 hours at 250–280° C.), high $T_g$ after cure (>300° C.), excellent thermal stability after cure (no weight loss after 132 hours at 265° C. in flowing air) and good combination of mechanical properties after cure (bases on qualitative assessment).

BRIEF DESCRIPTION OF THE DRAWING

For a more complete understanding of the present invention, including its objects and attending benefits, reference should be made to the Description of the Preferred Embodiments, which is set forth in detail below. This Detailed Description should be read together with the accompanying drawings, wherein.

DESCRIPTION OF THE PREFERRED EMBODIMENTS

Figure 1:
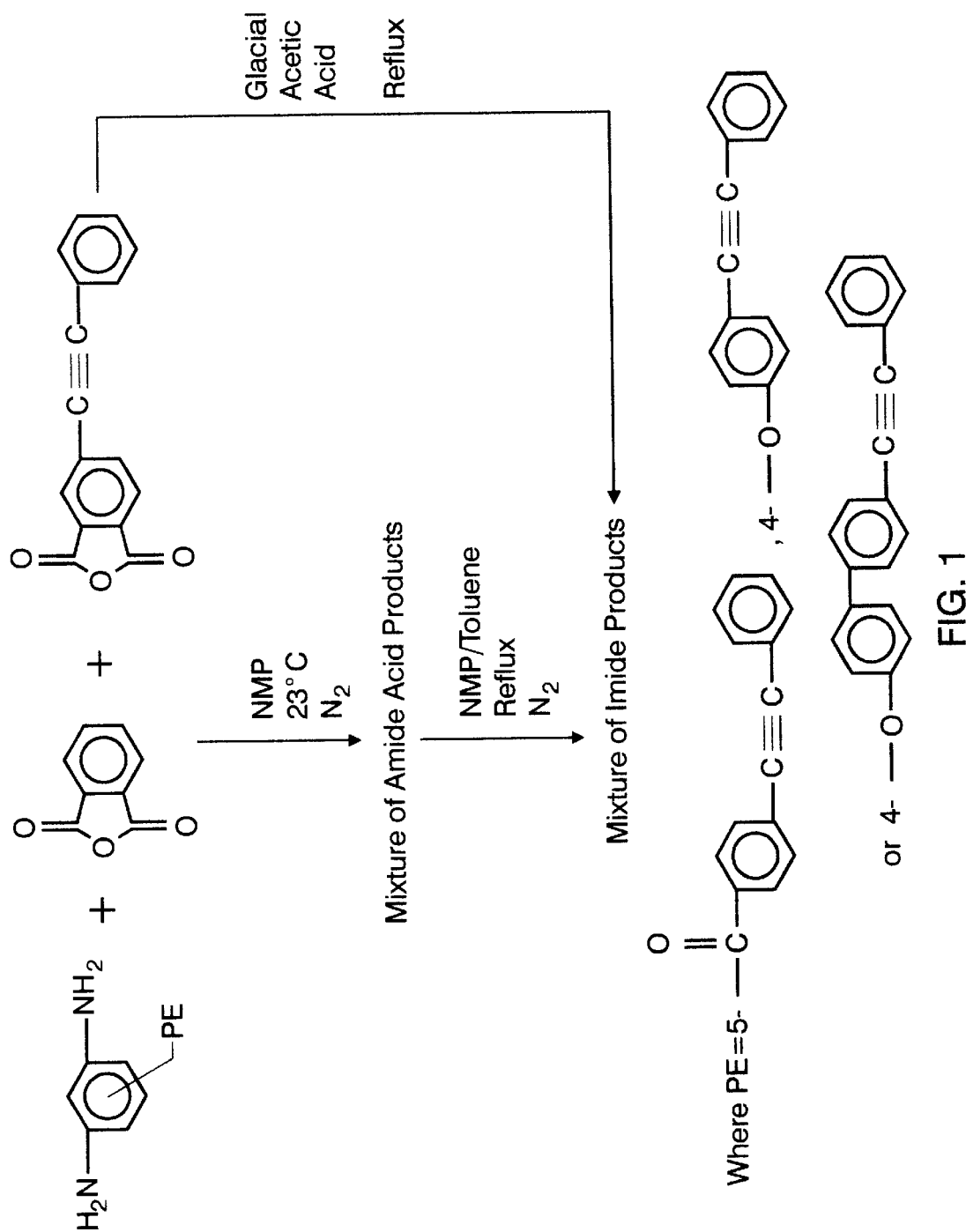
FIG. 1 is an equation showing the preparation of phenylethynyl reactive additives according to the present invention.

High temperature transfer molding resins (TMR) are prepared from aromatic diamines containing phenylethynyl groups and various ratios of phthalic anhydride (PA) and 4-phenylethynyl phthalic anhydride (PEPA) as shown in the equation of FIG. 1.

In one aspect, the present invention is a mixture of imide oligomers containing phenylethynyl groups, in any proportion, and consisting of the general chemical formula

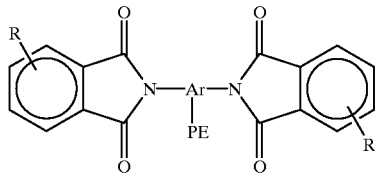

wherein Ar represents any aromatic group, PE is a radical represented by

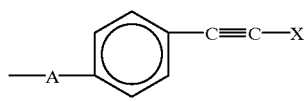

wherein A is a group comprising O, CO, $SO_2$ or

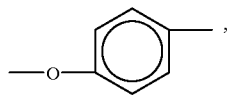

X is a substituted or unsubstituted aryl, and R is a hydrogen or any phenylethynyl group represented by —C≡C—X.

In another aspect the present invention is a process for synthesizing imide oligomers containing the phenylethynyl group by reacting 3,5-diamino-4'-phenylethynylbenzophenone and any proportion of a 4-phenylethynylphthalic anhydride and phthalic anhydride. By using this approach where ratios of PA and PEPA are used, a mixture of products is formed which consequently exhibit a lower melting temperature than that of the single product obtained by reacting the diamine with either PA or PEPA. For example, the product obtained from the reaction of 3,5-diamino-4'-phenylethynylbenzophenone and PA in refluxing acetic acid exhibits a melting point of 278° C. and the product from the same diamine and PEPA in refluxing acetic acid has a melting point of 252° C. The product from the reaction of this diamine and an equimolar ratio of PA and PEPA in refluxing acetic acid has a melting point of 182° C. The lower melting temperature is advantageous in these systems since it effectively provides a larger processing window between melting or softening temperature (i.e., onset of flow) and the temperature of onset of the thermal reaction of the phenylethynyl groups which rapidly decreases melt flow. The temperature of onset of the thermal reaction of the phenylethynyl groups (as determined by DSC in a sealed aluminum pan at a heating rate of 20° C./min) generally occurs ~335–350° C. The compounds are prepared in near quantitative yield in one step by an aromatic diamine containing phenylethynyl groups with a mixture of a phenylethynyl containing anhydride and a non-phenylethynyl containing anhydride in refluxing acetic acid. All the products from this reaction contain at least one phenylethynyl group.

The best results are obtained with the transfer molding material prepared from 3,5-diamino-4'-phenylethynylbenzophenone (1.0 mole), PA (1.0 mole) and PEPA (1.0 mole) in refluxing acetic acid (designated TMR-1). Transfer molding materials prepared from 3,5-diamino-4'-phenylethynylbenzophenone and different ratios of PA and PEPA, for example, PA (1.5 mole) and PEPA (0.5 mole) or PA (0.5 mole) and PEPA (1.5 mole) were also prepared (designated TMR-2 and TMR-3, respectively).

All of above compounds exhibit relatively low melting temperatures. TMR-2 and TMR-3 exhibit two melting transitions by DSC. The onset of the thermal reaction of the phenylethynyl groups occurred ~340° C. and reached a maximum at ~380° C. After curing for one hour at 350° C. in a sealed aluminum pan, no $T_g$s were detectable by DSC. In addition, no residual exothermic transitions or crystalline melting transitions were detected. This information suggests that after this thermal cure, these materials had a moderate to high degree of crosslinking and were fully cured. Thermomechanical analysis (TMA) of a piece of molding prepared from TMR-1 that had been cured for 1 hour at 350° C. indicated a $T_g$ of ~320° C. Thermogravimetric analyses (TGA) of uncured imide powders of these materials indicated temperatures of 5% weight loss of ~500° C. in air and ~525° C. in nitrogen. These results are comparable to those typically exhibited by aromatic polyimides. Isothermal gravimeteric analysis (ITGA) of a piece of molding prepared from TMR-1 and cured for one hour at 350° C. in air indicated no weight loss after 132 hours at 265° C. in flowing air. ITGA performed on this molding at 350° C. in air indicated a 50% weight loss after 132 hours in flowing air. For comparative purposes, a phenylethynyl terminated imide oligomer with a number average molecular weight of 5000 g/mole exhibited a 10% weight loss after 132 hours at 350° C. in air [See J. A. Hinkley and B. J. Jensen, *High Perf. Polym.* Vol. 7, 1–9 (1995)].

In addition, melt rheology was performed on the uncured powder of TMR-1.

Figure 2:
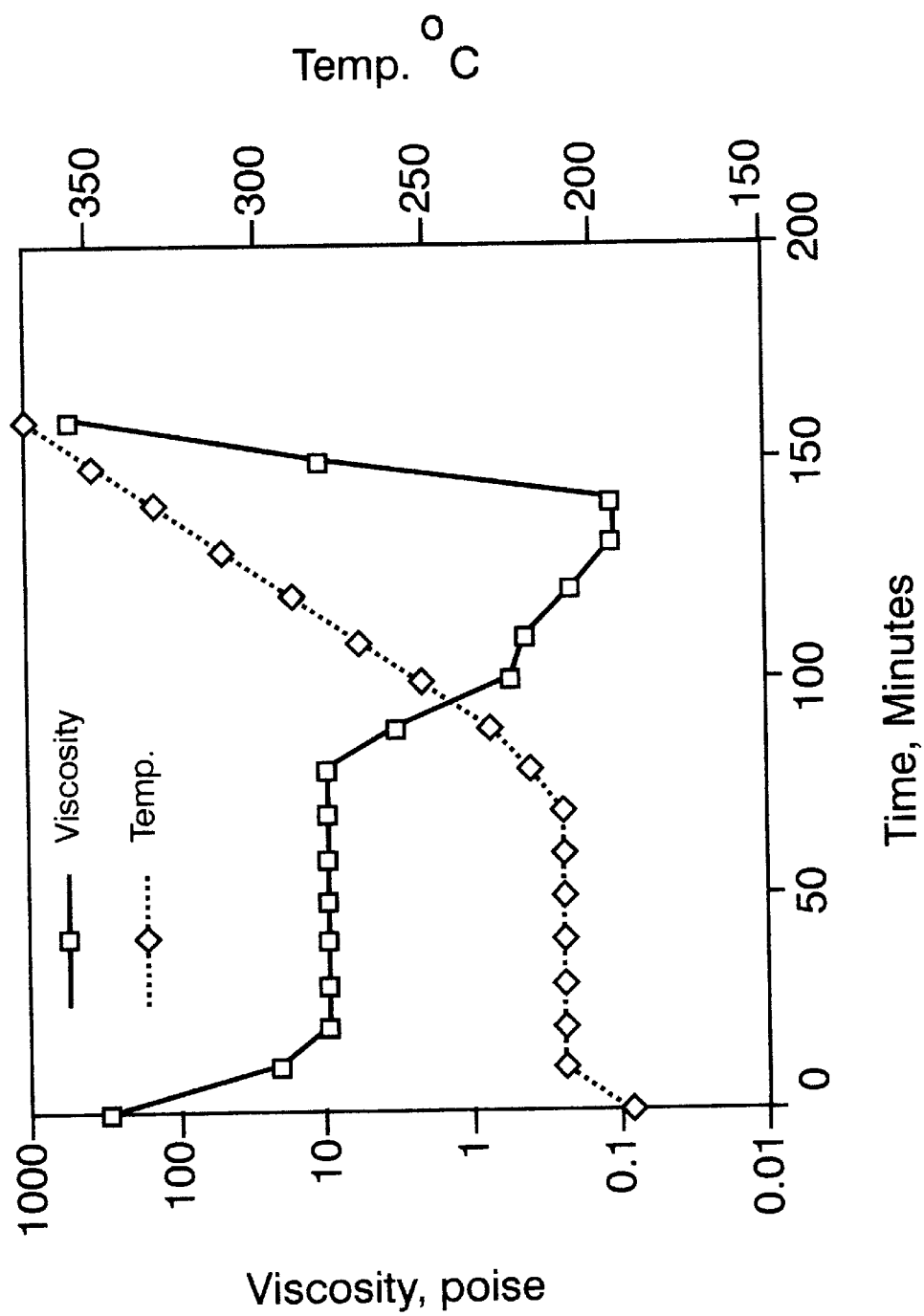
FIG. 2 is a melt viscosity profile of the uncured powder of 3,5-diamino-4'-phenylethynylbenzophenone (1.0 mole), PA (1.0 mole) and PEPA (1.0 mole).

The material was heated to ~210° C. and exhibited a complex melt viscosity of ~10 poise. There was no change in the complex viscosity after a one hour hold at this temperature. The material was subsequently heated to 350° C. over an additional 2 hour period. The complex melt viscosity decreased to less than 1.0 poise at ~240° C. and to 0.1 poise at ~270° C. The complex melt viscosity did not increase until the temperature reached ~325° C. corresponding to a time of ~2.5 hours after the material was first heated to 210° C. A graph of the melt viscosity versus temperature and time is presented in FIG. 2.

Having generally described the invention, a more complete understanding thereof can be obtained by reference to the following examples, which are provided herein for purposes of illustration only and do not limit the invention.

Synthesis of Transfer Molding Resins (TRMs)

EXAMPLE 1

Synthesis of TRM-1 from 3,5-diamino-4'-phenylethynylbenzophenone (1.0 mole), phthalic anhydride (1.0 mole) and 4-phenylethynylphthalic anhydride (1.0 mole)

Into a 3 L three-necked round-bottom flask equipped with a mechanical stirrer, thermometer and reflux condenser was placed 3,5-diamino-4'-phenylethynylbenzophenone (187.4 g, 0.60 mole), phthalic anhydride (88.9 g, 0.60 mole), 4-phenylethynylphthalic anhydride (148.9 g, 0.60 mole) and glacial acetic acid (785 mL, 34% solids). The mixture was heated to reflux (~120° C.) to give a dark brown solution. After ~2 hours at this temperature a large amount of light tan precipitate formed making stirring impossible. Heating was continued for 1 additional hour and the reaction mixture was cooled to room temperature. The product was isolated by filtration and washed three times in warm water to remove residual acetic acid. The solid was air dried overnight and most of the next day and subsequently placed in a forced air oven at 125° C. overnight. The light tan powder (397 g, 98% of theoretical yield), exhibited a melting transition at ~182° C., and an exothermic transition due to the thermal reaction of the phenylethynyl groups beginning at 346° C. and peaking at 381° C. as determined by DSC. The heat of reaction was ~275 J/g.

EXAMPLE 2

Synthesis of TRM-2 from 3,5-diamino-4'-phenylethynylbenzophenone (1.0 mole), phthalic anhydride (1.5 mole) and 4-phenylethynylphthalic anhydride (0.5 mole)

Into a 500 mL three-necked round-bottom flask equipped with a mechanical stirrer, thermometer and reflux condenser was placed 3,5-diamino-4'-phenylethynylbenzophenone (23.43 g, 75.0 mmole),), phthalic anhydride (16.66 g, 112.5 mmole), 4-phenylethynylphthalic anhydride (9.31 g, 37.5 mmole) and glacial acetic acid (125 mL, 30% solids). The mixture was heated to reflux (~120° C.) to give a dark brown solution. After ~2 hours at this temperature a large amount of light tan precipitate formed making stirring impossible. Heating was continued for 1 additional hour and the reaction mixture was cooled to room temperature. The product was isolated by filtration and washed three times in warm water to remove residual acetic acid. The solid was air dried overnight and subsequently placed in a forced air oven at 130° C. for six hours. The light tan powder (45.0 g, 96% of theoretical yield), exhibited a melting transition at ~179° C. and 235° C., and an exothermic transition due to the thermal reaction of the phenylethynyl groups beginning at 346° C. and peaking at 383° C. as determined by DSC. The heat of reaction was ~209 J/g.

EXAMPLE 3

Synthesis of TRM-3 from 3,5-diamino-4'-phenylethynylbenzophenone (1.0 mole), phthalic anhydride (0.5 mole) and 4-phenylethynylphthalic anhydride (1.5 mole)

Into a 500 mL three-necked round-bottom flask equipped with a mechanical stirrer, thermometer and reflux condenser was placed 3,5-diamino-4'-phenylethynylbenzophenone (21.98 g, 70.4 mmole), phthalic anhydride (5.21 g, 35.2 mmole), 4-phenylethynylphthalic anhydride (26.20 g, 105.5 mmole) and glacial acetic acid (200 mL). The mixture was heated to reflux (~120° C.) to give a dark brown solution. After ~2 hours at this temperature a large amount of light tan precipitate formed making stirring impossible. Heating was continued for 1 additional hour and the reaction mixture was cooled to room temperature. The product was isolated by filtration and washed three times in warm water to remove residual acetic acid. The solid was air dried overnight and subsequently placed in a forced air oven at 130° C. for six hours. The light tan powder (50.2 g, 99% of theoretical yield), exhibited a melting transition at ~191° C. and 230° C., and an exothermic transition due to the thermal reaction of the phenylethynyl groups beginning at 340° C. and peaking at 374° C. as determined by DSC.

While the invention has been described in terms of its preferred embodiments, those skilled in the art will recognize that the invention can be practiced with modification within the spirit and scope of the appended claims.

We claim:
1. An imide compound having the general chemical formula:

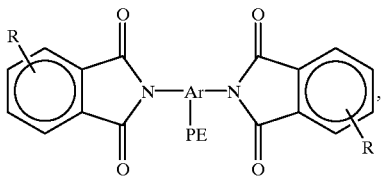

wherein Ar represents any aromatic group,
wherein PE is radical represented by

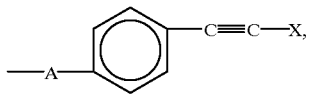

wherein A is a radical selected from the group consisting of O, CO, $SO_2$ and

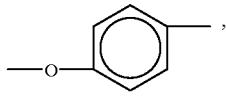

wherein X is selected from the group consisting of substituted aryl group and unsubstituted aryl group,
wherein R is selected from the group consisting of hydrogen and any phenylethynyl group represented by —C≡C—X.

2. An imide compound obtained by reacting an aromatic diamine containing phenylethynyl groups having the general chemical formula

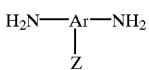

wherein Z is a radical selected from the group consisting of

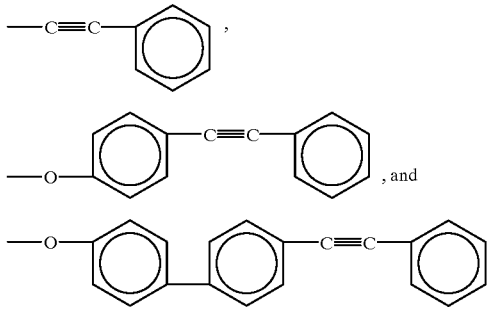

wherein Ar represents any aromatic group, with any proportion of a phenylethynyl containing anhydride and a non-phenylethynyl containing anhydride.

3. A mixture of imide compounds obtained by reacting 3,5-diamino-4'-phenylethynylbenzophenone and any proportion of a 4-phenylethynylphthalic anhydride and phthalic anhydride.

4. The mixture of imide compounds of claim 3, wherein the reaction is carried out in glacial acetic acid.

5. A process of synthesizing a mixture of imide compounds containing at least one phenylethynyl group and having the general structural formula according to claim 1

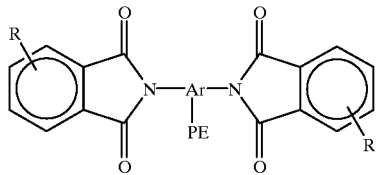

which process comprises the reaction between 3,5-diamino-4'-phenylethynylbenzophenone and any proportion of a 4-phenylethynylphthalic anhydride and phthalic anhydride.

6. A process of synthesizing a mixture of imide compounds containing at least one phenylethynyl group and having the general structural formula according to claim 1

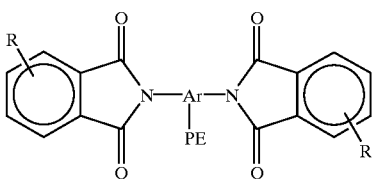

which process comprises the reaction between 3,5-diamino-4'-phenylethynylbenzophenone and any proportion of a 4-phenylethynylpthalic anhydride and phthalic anhydride in glacial acetic acid.

7. A composite prepared from the imide compound according to claim 1.

* * * * *